(12) United States Patent
Yuan et al.

(10) Patent No.: US 10,083,397 B2
(45) Date of Patent: Sep. 25, 2018

(54) PERSONALIZED INTELLIGENT WAKE-UP SYSTEM AND METHOD BASED ON MULTIMODAL DEEP NEURAL NETWORK

(71) Applicant: TCL RESEARCH AMERICA INC., San Jose, CA (US)

(72) Inventors: Jianbo Yuan, San Jose, CA (US); Haohong Wang, San Jose, CA (US); Xiaobo Ren, San Jose, CA (US)

(73) Assignee: TCL RESEARCH AMERICA INC., San Jose, CA (US)

( * ) Notice: Subject to any disclaimer, the term of this patent is extended or adjusted under 35 U.S.C. 154(b) by 135 days.

(21) Appl. No.: 15/247,665

(22) Filed: Aug. 25, 2016

(65) Prior Publication Data

US 2018/0060732 A1    Mar. 1, 2018

(51) Int. Cl.
| | |
|---|---|
| *G08B 1/00* | (2006.01) |
| *G06N 5/02* | (2006.01) |
| *G06N 3/08* | (2006.01) |
| *G08B 3/10* | (2006.01) |
| *A61B 5/00* | (2006.01) |

(52) U.S. Cl.
CPC .............. *G06N 5/02* (2013.01); *A61B 5/4812* (2013.01); *G06N 3/08* (2013.01); *G08B 3/10* (2013.01)

(58) Field of Classification Search
CPC ............... G06N 5/02; G06N 3/08; G08B 3/10
USPC ................... 340/573.1, 309.1, 539.1, 539.11
See application file for complete search history.

(56) References Cited

U.S. PATENT DOCUMENTS 5,400,246 A * 3/1995 Wilson .................... G06F 3/023
340/12.53

* cited by examiner

*Primary Examiner* — Daryl Pope
(74) *Attorney, Agent, or Firm* — Anova Law Group, PLLC

(57) ABSTRACT

A method for personalized intelligent wake-up system based on multimodal deep neural network comprises monitoring a sleeping status of a user; obtaining a current sleeping-stage of the user within a current time frame and a prediction of a next sleeping-stage of the user for a next time frame; correcting the current sleeping-stage of the user through combining the current sleeping-stage and the prediction of the next sleeping-stage; determining a wake up strategy for the current time frame; determining a relationship between each of a plurality of alarm impulses adopted to wake up the user and a corresponding reaction of the user; identifying a change in the current sleeping-stage for the current time frame; determining an alarm impulse to be triggered for waking up the user; and triggering the determined alarm impulse.

20 Claims, 8 Drawing Sheets

PERSONALIZED INTELLIGENT WAKE-UP SYSTEM AND METHOD BASED ON MULTIMODAL DEEP NEURAL NETWORK

FIELD OF THE INVENTION

The present invention relates generally to the field of computer technologies and, more particularly, to a personalized intelligent wake-up system and method based on multimodal deep neural network.

BACKGROUND

Sleep is a very important part of human's daily life, and sleep quality has a great impact on various aspects of one's metal and physical status, such as one's fatigue, mood, attention, and concentration, etc. High quality sleep can make a big difference in one's quality of life. Therefore, it is important and highly desired to optimize the way to wake people up. In existing intelligent sleep management systems or alarm management systems, a general system framework often includes a sensor input module to monitor a user's sleeping-stage and a decision making module to decide when to trigger an alarm.

The current so-called "intelligent" systems may not be real intelligent systems because they are unable to find a personally optimized wake-up solution for each user. The most commonly used strategy for the decision module is to set up a wake-up threshold and trigger the alarm when the user's sleeping-stage reaches a wake-up threshold within a time frame (usually thirty minutes before) of the user-set alarm time.

However, when a user is in deep sleep during the wake-up time frame, such strategy may be unable to find a sweet spot to trigger the alarm, and the user may be forced to wake up from his or her deep sleep when the time is running out. Even when the existing intelligent sleep management systems or alarm management systems do find a good wake-up point when the user's sleep stage hits the threshold, the wake-up point may not be guaranteed to be the optimized wake up point because the user may go back to deep sleep again. In addition, different users may prefer different wake-up thresholds.

Thus, the existing intelligent sleep management systems or alarm management systems may not be configured with personalized settings, i.e., the existing intelligent sleep management systems or alarm management systems may not be personalized. Moreover, the existing intelligent sleep management systems or alarm management systems are based on monitoring the user's sleeping-stage from sensor data (e.g., data collected by cellphones, wearable band, etc.), which may be very noisy and unreliable.

The disclosed systems and methods are directed to solve one or more problems set forth above and other problems.

BRIEF SUMMARY OF THE DISCLOSURE

One aspect of the present disclosure includes a method for a personalized intelligent wake-up system based on multimodal deep neural network. The method comprises monitoring a sleeping status of a user; obtaining a current sleeping-stage of the user within a current time frame and a prediction of a next sleeping-stage of the user for a next time frame; correcting the current sleeping-stage of the user through combining the current sleeping-stage and the prediction of the next sleeping-stage; based on the current sleeping-stage of the user, prior knowledge learnt from sleep-related research studies, and at least one user preference of waking up, determining a wake up strategy for the current time frame; determining a relationship between each of a plurality of alarm impulses adopted to wake up the user and a corresponding reaction of the user; identifying a change in the current sleeping-stage for the current time frame; based on the wake-up strategy established for the current time frame and the relationship between each of the plurality of alarm impulses and the reaction of the user, determining an alarm impulse to be triggered for waking up the user; and triggering the determined alarm impulse.

Another aspect of the present disclosure includes a personalized intelligent wake-up system based on multimodal deep neural network. The system comprises a robust sleeping-stage detection (RSSD) module configured to monitor a sleeping-stage of a user, obtain a current sleeping-stage of the user within a current time frame, predict a next sleeping-stage of the user for a next time frame, and correct the current sleeping-stage of the user; a wake-up strategy (WS) module configured to receive to establish a wake-up strategy for the current time frame, based on the current sleeping-stage of the user, prior knowledge learnt from sleep-related research studies, and at least one user preference of waking up; an alarm and user reaction regression (AUR) module configured to determine a relationship between each of a plurality of alarm impulses adopted to wake up the user and a corresponding reaction of the user; and a decision fusion (DF) module configured to determine an alarm impulse to be triggered based on the wake-up strategy established for the current time frame and the relationship between each of the plurality of alarm impulses and the reaction of the user, and configured to trigger the alarm impulse.

Another aspect of the present disclosure includes a non-transitory computer-readable medium having computer program for, when being executed by a processor, performing a method for a personalized intelligent wake-up system based on multimodal deep neural network. The method comprises monitoring a sleeping status of a user; obtaining a current sleeping-stage of the user within a current time frame and a prediction of a next sleeping-stage of the user for a next time frame; correcting the current sleeping-stage of the user through combining the current sleeping-stage and the prediction of the next sleeping-stage; based on the current sleeping-stage of the user, prior knowledge learnt from sleep-related research studies, and at least one user preference of waking up, determining a wake up strategy for the current time frame; determining a relationship between each of a plurality of alarm impulses adopted to wake up the user and a corresponding reaction of the user; identifying a change in the current sleeping-stage for the current time frame; based on the wake-up strategy established for the current time frame and the relationship between each of the plurality of alarm impulses and the reaction of the user, determining an alarm impulse to be triggered for waking up the user; and triggering the determined alarm impulse.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

DETAILED DESCRIPTION

Reference will now be made in detail to exemplary embodiments of the invention, which are illustrated in the accompanying drawings. Hereinafter, embodiments consistent with the disclosure will be described with reference to drawings. Wherever possible, the same reference numbers will be used throughout the drawings to refer to the same or like parts. It is apparent that the described embodiments are some but not all of the embodiments of the present invention. Based on the disclosed embodiments, persons of ordinary skill in the art may derive other embodiments consistent with the present disclosure, all of which are within the scope of the present invention.

Figure 3:
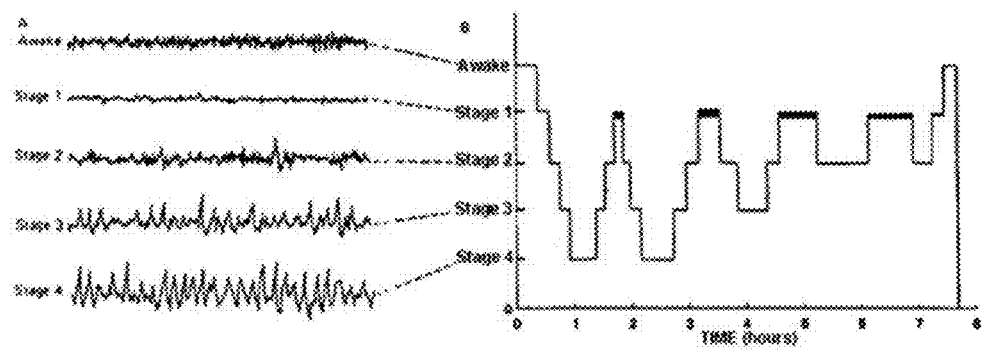
FIG. 3 illustrates a typical person's sleep stages through the night.

People often experience two different phases of sleeps during the night: Rapid Eye Movement (REM) sleep and non-REM sleep, which may alternately appear through the night. The periodical rhythm of the REM and the non-REM sleeps are called a sleep cycle. Non-REM sleep can be subdivided into 4 sub-stages, in which each successive stage of non-REM sleep is indicative of a deeper sleep, with stage 1 as the lightest and stage 4 as the deepest. FIG. 3 illustrates a typical person's sleeping stages through the night. As shown in FIG. 3, a person may experience different sleep stages through the night.

Certain studies indicate that people feel more comfortable when they wake up in the REM sleep than in the non-REM sleep. However, certain other studies indicate that the first non-REM sleeping-stage is the ideal stage for waking people up. As discussed above, the existing intelligent sleep management systems or alarm management systems often focus on monitoring the user's sleeping-stage from sensor data (e.g., data collected by cellphones, wearable band, etc.), which may be substantially unreliable and may not be configured with personalized settings.

The present disclosure provides a personalized intelligent wake-up system based on multimodal deep neural network between an alarm impulse and user specific reactions, which may be able to find a personalized and optimized way to wake up each user. Accordingly, even if the users are in deep sleep, the disclosed intelligent wake-up system may gently bring the users from deep sleep to light sleep, providing a better wake up solution.

For example, if a user is in a deep sleep stage, the disclosed intelligent wake-up system may gently bring the user to a light sleep stage and to be ready for waking up without a "hard alarm". As contrary, the existing intelligent sleep management systems or alarm management systems often use the "hard alarm", i.e., trigger a loud alarm, to wake up the user when the time is running out while the user is still in the deep sleep stage.

Figure 1:
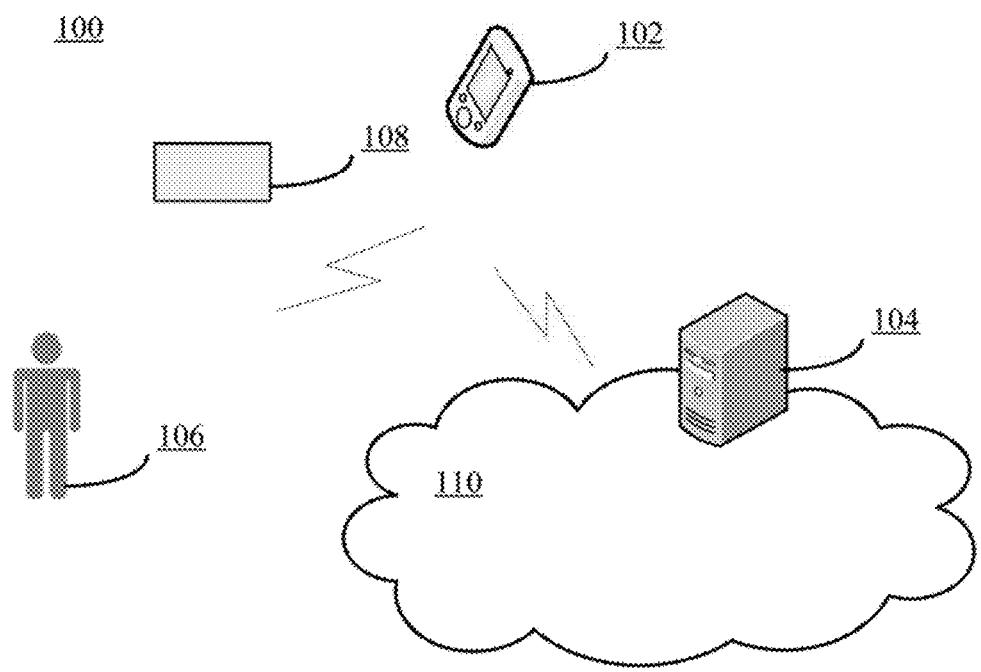
FIG. 1 illustrates an exemplary environment incorporating certain embodiments of the present invention.

FIG. 1 illustrates an exemplary environment 100 incorporating certain embodiments of the present invention. As shown in FIG. 1, the environment 100 may include a user terminal 102, a server 104, a user 106, a sensor 108, and a network 110. Other devices may also be included.

The user terminal 102 may include any appropriate type of electronic device with computing capabilities, such as TVs (smart TVs or non-smart TVs), a smart watch, a mobile phone, a smartphone, a tablet, a personal computer (PC), a server computer, a laptop computer, and a digital personal assistant (PDA), etc.

The server 104 may include any appropriate type of server computer or a plurality of server computers for providing personalized contents to the user 106. For example, the server 104 may be a cloud computing server. The server 104 may also facilitate the communication, data storage, and data processing between the other servers and the user terminal 102. The user terminal 102, and server 104 may communicate with each other through one or more communication networks 110, such as cable network, phone network, and/or satellite network, etc.

The user 106 may interact with the user terminal 102 to query and to retrieve various contents and perform other activities of interest, or the user may use voice, hand or body gestures to control the user terminal 102 if speech recognition engines, motion sensor or depth-camera is used by the user terminal 102. The user 106 may be a single user or a plurality of users, such as family members.

The sensor 108 may be an internal sensor of the user terminal 102 and/or server 104, or may be an external sensor connected to the user terminal 102 and/or server 104 over the network 110. The sensor 108 may be a wearable band capable of tracking user's body movements in the bed, recording information of vital body functions like breathing, heartbeat through the night. The sensor 108 may also be a camera capable of monitoring user's body movements and providing physical body positions of the user. Further, the sensor 108 may be any appropriate type of sensors capable of tracking user's sleeping status through various ways.

Figure 2:
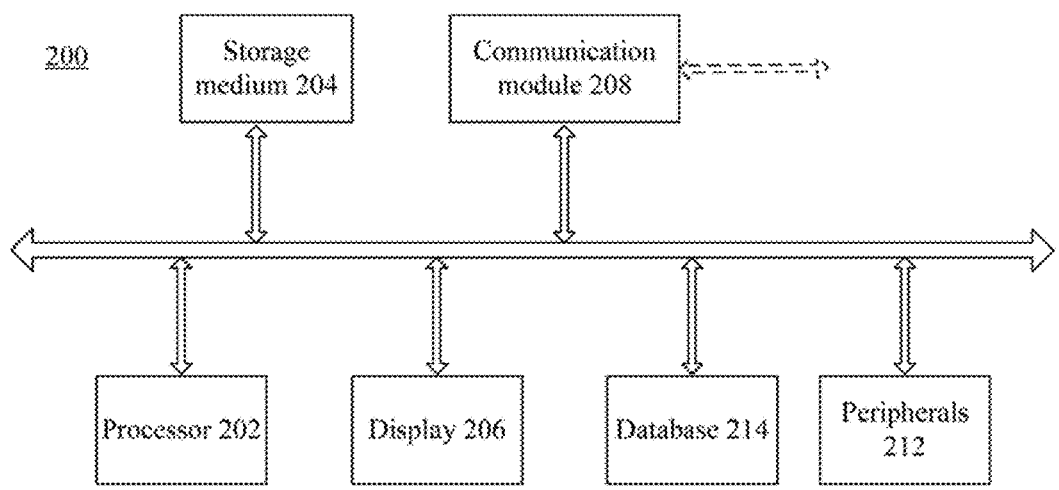
FIG. 2 illustrates an exemplary computing system consistent with disclosed embodiments.

The user terminal 102, and/or server 104 may be implemented on any appropriate computing circuitry platform. FIG. 2 shows a block diagram of an exemplary computing system capable of implementing the user terminal 102, and/or server 104.

As shown in FIG. 2, the computing system 200 may include a processor 202, a storage medium 204, a display 206, a communication module 208, a database 214, and peripherals 212. Certain components may be omitted and other components may be included.

The processor 202 may include any appropriate processor or processors. Further, the processor 202 can include multiple cores for multi-thread or parallel processing. The storage medium 204 may include memory modules, such as ROM, RAM, flash memory modules, and mass storages, such as CD-ROM and hard disk, etc. The storage medium 204 may store computer programs for implementing various processes, when the computer programs are executed by the processor 202.

Further, the peripherals 212 may include various sensors and other I/O devices, such as keyboard and mouse, and the communication module 208 may include certain network interface devices for establishing connections through communication networks. The database 214 may include one or more databases for storing certain data and for performing certain operations on the stored data, such as database searching.

Figure 4:
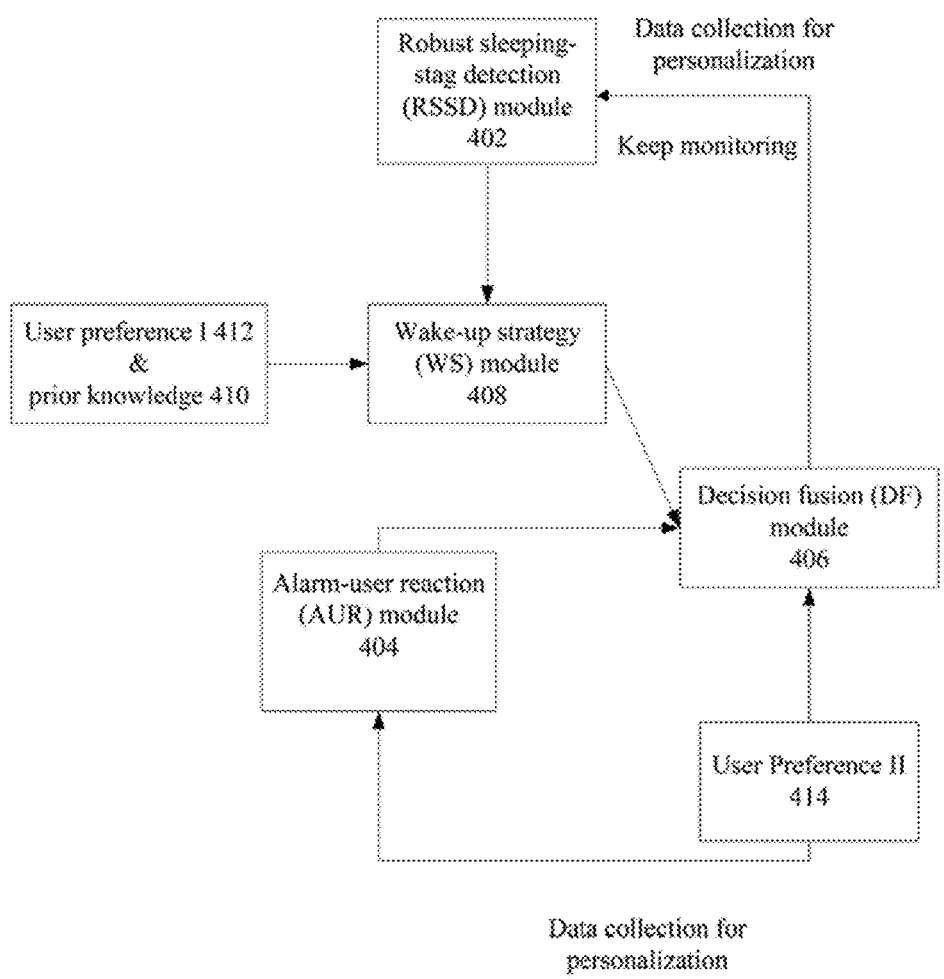
FIG. 4 illustrates an exemplary personalized intelligent wake-up system based on multimodal deep neural network consistent with disclosed embodiments.

FIG. 4 illustrates an exemplary a personalized intelligent wake-up system based on multimodal deep neural network consistent with disclosed embodiments. As shown in FIG. 4, the personalized intelligent wake-up system 400 may include a robust sleeping-stage detection (RSSD) module 402, an alarm and user reaction regression (AUR) module 404, a decision fusion (DF) module 406, and a wake-up strategy (WS) module 408. Certain components may be omitted and other components may be added.

For all intelligent sleep and alarm management systems, it's very important to find a way to monitor user's sleeping-stage and status. The user's sleeping status is often used for determining whether to trigger the alarm in most of such systems. However, as discussed above, in the current intelligent sleep and alarm management systems, the whole sleeping-stage monitoring is based on sensor data, which may be very noisy and unreliable.

For example, some intelligent sleep and alarm management systems place a smart phone facing down on the bed and use the smart phone to sense the user's body movement in bed. However, the sensors in smart phones may not be sensitive enough for an accurate monitoring. Some intelligent sleep and alarm management systems use a mic to monitor the user's body movement through collecting audios around, which may be highly dependent on the environment set-up and may be not reliable all the time.

Moreover, the ways to monitor user's sleeping-stage and status methods may follow a unified standard for determining which sleeping-stage the user is in. However, the unified standard may not be always true, because some users may behave differently in the same sleeping-stage, such as fewer or more body movements. For example, the user may have fewer body movement if he/she is very tired, the user may have more body movement if he/she doesn't sleep well due to an environment change.

Thus, as shown in FIG. 4, the disclosed personalized intelligent wake-up system 400 may include the robust sleeping-stage detection (RSSD) module 402, which may be configured to perform a robust monitoring on the user's sleeping-stage based on sensor data, and correct the users' sleeping-stage by combining the sensor data with a sleeping-stage prediction based on historical data. That is, the user's sleeping-stage may be inferred from monitoring sensor data, and further corrected with a sleeping-stage prediction module based on historical data.

Figure 5:
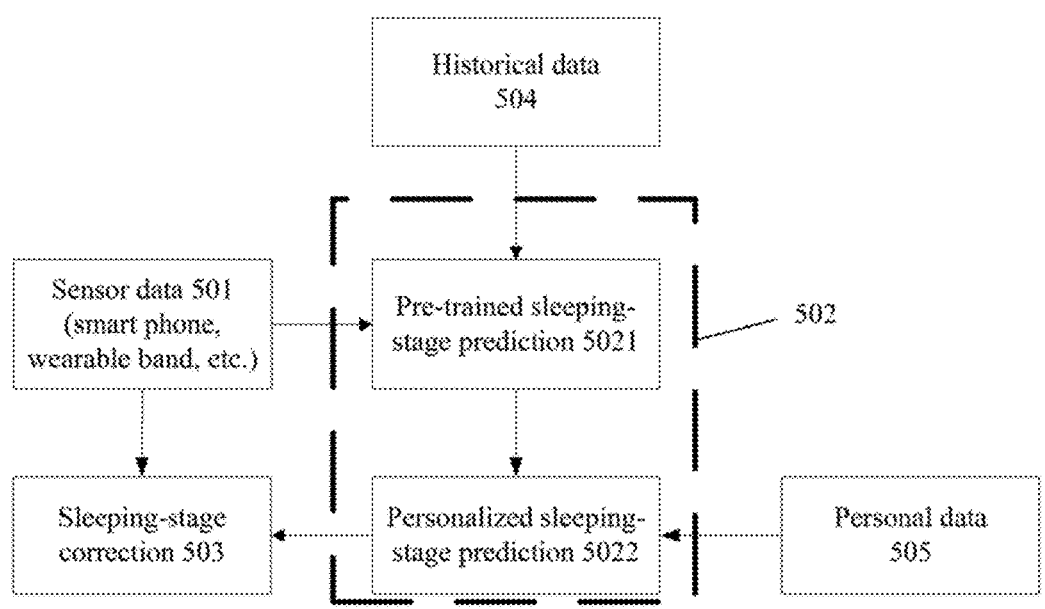
FIG. 5 illustrates an exemplary process of an exemplary robust sleeping-stage detection (RSSD) module consistent with disclosed embodiments.

FIG. 5 illustrates an exemplary robust sleeping-stage detection (RSSD) module consistent with disclosed embodiments. As shown in FIG. 5, the RSSD module may be configured to monitor the user's sleeping-stage, obtain the user's current sleeping-stage within a current time frame based on sensor data 501, perform a sleeping-stage prediction 502 for a next time frame, and perform a sleeping-stage correction 503 through combining the sensor data 501 and the sleeping-stage prediction 502 in a late fusion fashion. In particular, the sleeping-stage prediction 502 may include a pre-trained sleeping-stage prediction 5021 based on historical data 504 and a personalized sleeping-stage prediction 5022 based on personal data 505.

The sensor data 501 maybe provided by, for example, a smart phone or a wearable band capable of sensing the user's body movement in bed. The sensor data 501 may include certain noise caused by, for example, by the corresponding sensors. The historical data 504 may include data of the user's sleeping status for the past several days or months, for example, how long each sleeping-stage lasts, when the user wake up, etc. The historical data 503 may be pre-processed to remove the noise, thus, the historical data 503 may be more reliable than the sensor data 501.

The previous sleeping-stage data (i.e., historical data 504) may be collected for training purposes. The historical data 504 of general users may be collected for pre-training, i.e., for realizing the pre-trained sleeping-stage prediction 5021. The personal data 505, collected from a specific user may be input to the RSSD module 402 for fine-tuning the personalized sleeping-stage prediction 5022.

It should be noted that, the RSSD module 402 may also work without the personalized sleeping-stage prediction 5022 (i.e., the user may turn on/off "personalized sleeping-stage prediction 5022") and even without the sleeping-stage prediction 502. However, to achieve a desired performance of robust sleeping-stage monitoring, the RSSD module may be highly desired to have the personalized sleeping-stage prediction 5022 and the sleeping-stage prediction 502 turned on.

Returning to FIG. 4, the WS module 408 may be configured to receive the inferred user's sleeping-stage, prior knowledge 410, and user preference I 412 as inputs, to establish a desired wake-up strategy (WS) for the current time frame. The prior knowledge 410 may be prior knowledge learnt from sleep-related research studies. The user preference I 412 may include various user preferences of waking up, for example, the user may prefer to wake up during light sleep, or prefer a quick wakeup, etc. The user preference I 412 may be received in various ways, for example, manually inputted by the user, provided by a monitoring sensor (e.g., user's cell phone, wearable devices, etc.), acquired by analyzing user's activities on social medium, selected from a dropdown list or clicking icons provided by the system, etc.

The WS module 408 may also be configured to determine an alarm impulse for performing a gentle and optimized bring-up on the user's sleeping-stage. The alarm impulse may refer to an impulse for waking the user up. The alarm impulse may be a sound alarm, a vibration, a combination of a sound alarm and a vibration, etc. The WS module 408 may also be configured to determine various configuration of the alarm impulse, for example, the alarm impulse's types, duration, strength, and repeating frequency, etc.

The AUR module 404 may be configured to determine a relationship between an alarm impulse (e.g., alarm, vibration, a combination of alarm and vibration, etc.) and a user's reaction (e.g., a change in the user's sleeping-stage and status). Alarm impulses of different types (e.g., alarm, vibration, a combination of alarm and vibration, etc.) and/or alarming in different ways (e.g., soft alarm, hard alarm, etc.) may lead to different user's reaction. The AUR module 404 may be configured to determine a relationship between each of a plurality alarm impulses and the user's reaction.

For example, the types of the song chosen as wake-up alarms (i.e., the types of song alarm 702) may lead to different user's reaction, because light music may slightly wake the user up while rock music may be too stronger for a certain group of users. In addition, the ways to play the song alarm, such as playing with low/high volume, playing from low volume to high volume, playing in high/low frequency, may also have an impact on the user experience and may receive different user responses. Environment background may have to be taken into account as well. A constant or random noise, raised when someone is taking a shower on the next door, or when a truck is passing by, may also be considered as an alarm impulse, which may also bring a change to the user's sleeping-stage. In one embodiment, the AUR module 404 may be configured to adopt a multimodal deep regression algorithm to model the relationship between the alarm impulse and the user's reaction.

Based on receiving the wake-up strategy (WS) determined by the WS module 408, and the relationship between the alarm impulse and the user's reaction determined by the AUR module 404, the DF module 406 may be configured to determine which specific impulse would be triggered, then trigger the alarm impulse. For example, the DF module 406 may be configured to determine which song to play, how to play the song, with or without vibration, how strong background noise is, etc.

User preference II 414 may provide alarm impulse candidates, for example, walk-up alarm songs, i.e., songs set as wake-up alarms. The user preference II 414 may also be fed into the DF module 406 to narrow down a searching range. For example, some users don't like the walk-up alarm songs to be played with a vibration, thus, such a vibration option may be removed from the user preference II 414. In addition, the user preference II 414 may also include song lists and ratings from the user's Spotify, such as Apple music, and local music data base, etc., facilitating the search for user's favorite walk-up alarm songs.

After a desired impulse is triggered, the personalized intelligent wake-up system based on multimodal deep neural network 400 may keep monitoring and correcting the user's sleeping-stage, and following the same framework flow until the user's final wake up.

Figure 9:
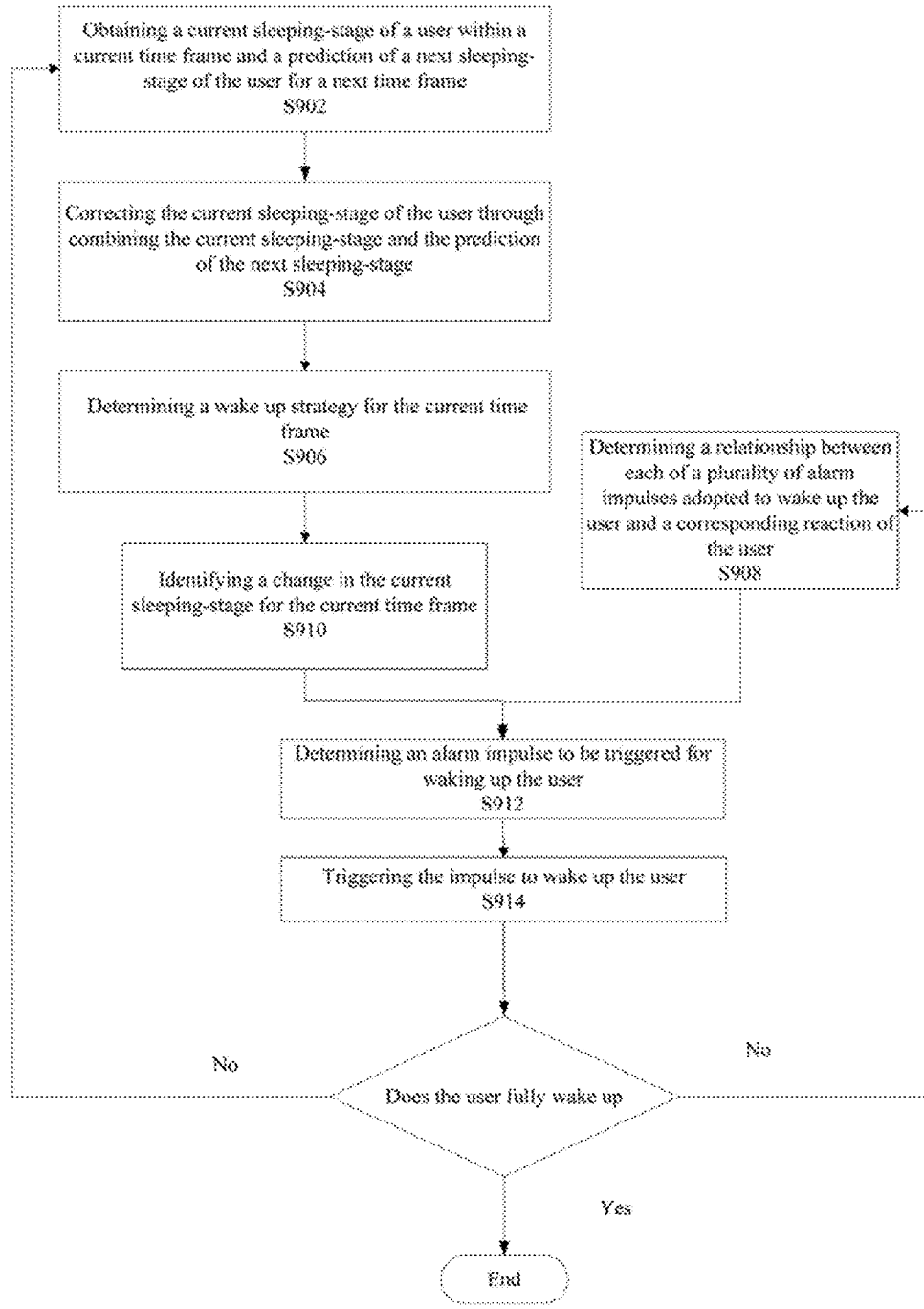
FIG. 9 illustrates a flow chart of an exemplary method for a personalized intelligent wake-up system based on multimodal deep neural network consistent with disclosed embodiments.

The present disclosure also provides a method for a personalized intelligent wake-up system based on multimodal deep neural network. FIG. 9 illustrates a flow chart of an exemplary method for a personalized intelligent wake-up system based on multimodal deep neural network consistent with disclosed embodiments. As shown in FIG. 9, at the beginning, a current user sleeping-stage within a current time frame and a prediction of user's sleeping-stage for a next time frame are obtained (S902).

In particular, the current user sleeping-stage (i.e., a current sleeping-stage result) may be obtained by monitoring sensor data, which may be provided by, for example, a smart phone or a wearable band capable of sensing the user's body movement in bed. The sleeping-stage prediction may be generated by the RSSD module based on a predetermined sleeping-stage prediction model and historical data of the user's sleeping status. For example, the historical data may include data of the user's sleeping status for the past several days or months, for example, how long each sleeping-stage lasts, when the user wake up, etc.

To pre-train and fine-tune (i.e., personalized) the sleeping-stage prediction model, deep learning algorithms may be adopted. In one embodiment, recursive neural networks (RNN) may be adopted to predict the sleeping-stage for the next time frame based on the user's previous and current sleeping-stage input. That is, the deep learning algorithm may work under a sequence-in sequence-out scenario. The previous sleeping-stage data (i.e., historical data) may be collected and fed into a RNN model for training purposes. The general collected data may be used for pre-training the sleeping-stage prediction model, while the data collected from a specific user may be used for fine-tuning the sleeping-stage prediction model.

Figure 6:
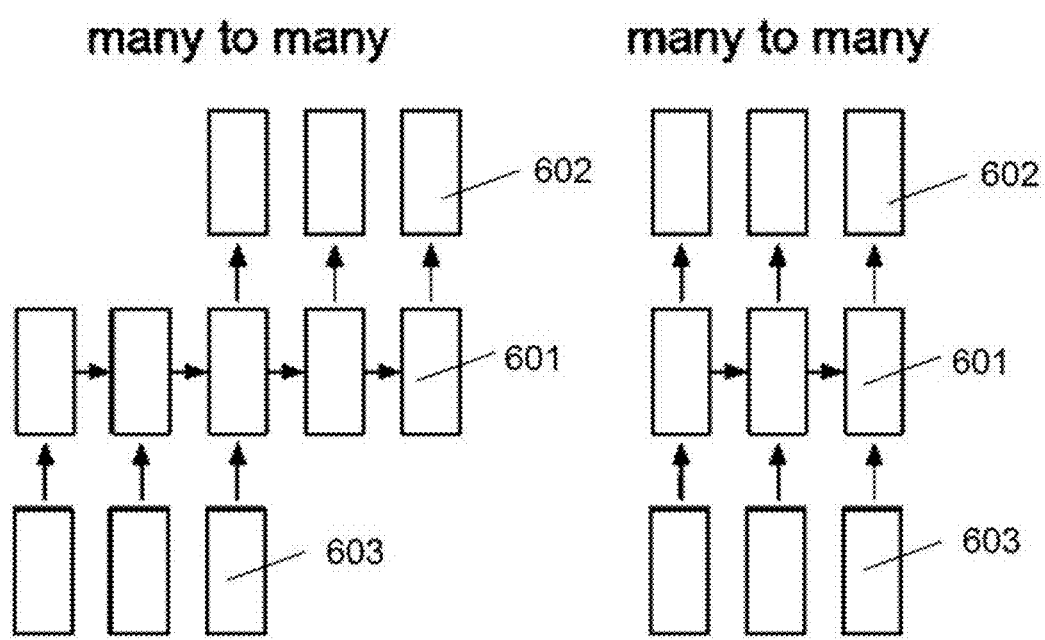
FIG. 6 illustrates an exemplary recursive neural networks (RNNs) for sleeping stage (sequence signal) prediction consistent with disclosed embodiments.

FIG. 6 illustrates an exemplary recursive neural networks (RNNs) for sleeping-stage (sequence signal) prediction consistent with disclosed embodiments. As shown FIG. 6, recursive neural networks (RNNs) may include a plurality of blocks 601, a plurality of blocks 602, and a plurality of blocks 603. Each block 601 may be a unit of RNNs, and the blocks 602 (red) and blocks 602 may be input and output sequence, respectively.

Returning to FIG. 9, after the current user sleeping-stage and the prediction of user sleeping-stage within the current time frame is obtained, the current sleeping-stage is corrected through combining the current sleeping-stage and the prediction of user's sleeping-stage in a late fusion fashion (S904).

Personal data ground truth may be hard to get directly, but the ground truth may be estimated, and the system may be tuned iteratively, which may eventually converge to the ground truth. For example, a wake-up point may be determined first, which may be easily identified when the user touches the screen to stop the alarm. Then the corrected sleeping-stage data after the fusion of the sensor data and the raw prediction may be scaled by a factor of the real wake-up stage (for example, according to the system the user is waken up at stage 4) and the theoretical wake-up stage (stage awake).

To be more specific, $S_{sensor}$ denotes a sleeping-stage inferred from the sensor data, and $S_{scaled}$ denotes a scaled prediction of sleeping-stage, and $\alpha$ denotes a weight, the output S of the RSSD module (i.e., the corrected current sleeping-stage) is written as follows:

$$S = \alpha S_{sensor} + (1-\alpha) S_{scaled} \quad (1)$$

The weight $\alpha$ is computed by comparing the difference among the last inference of sleeping-stage from sensor data $S_{s'}$, the last prediction of sleeping-stage from RNN model $S_{p'}$, and the wake-up point stage $S_{wake}$:

$$\alpha = \frac{S_{wake} - S_{p'}}{2S_{wake} - S_{p'} - S_{s'}} \quad (2)$$

Based on by the wake-up point stage $S_{wake}$, the stage prediction of the wake-up point from last available data point $S_{w'}$ (for example, data collected from "yesterday"), and the current prediction $S_{predict}$ outputted from the prediction model, the scaled prediction $S_{scaled}$ is calculated as:

$$S_{scaled} = \frac{S_{w'}}{S_{wake}} S_{predict} \quad (3)$$

That is, during a fusion of the sleeping-stage prediction is combined with the current sleeping-stage result, an adaptive weight of the two (i.e., the sleeping-stage prediction and the current sleeping-stage result) may be adopted to establish the robust result for sleeping-stage monitoring outputted to the WS module. The adaptive weight may be generated, for instance, by finding the wake-up point which is much easier and accurate to detect, and by comparing the difference among the wake-up point and the sleeping-stage inferred from the sensor data, and the sleeping-stage prediction. The one (i.e., one of the sleeping-stage prediction and the current sleeping-stage result) with a larger difference may be given a smaller weight accordingly.

After the current user's sleeping-stage is corrected, user preference I and prior knowledge are combined to determine an optimized wake up strategy for the user (S906). For example, the user is in deep sleep and his/her preference is to be waken up a little at a time. His/her preference may be used to find the best tradeoffs between the intervals of each alarm impulse and the level of each alarm impulse. On the other hand, if the user prefers a quick wakeup, the disclosed personalized intelligent wake-up system may adjust the wake-up strategy accordingly, applying relatively strong but smooth impulses to avoid hard feeling of being waken up from the deep sleep.

Based on the prior knowledge obtained from research studies regarding sleep and sleep quality, a best wake-up curve of sleeping stage for the user may be established. The prior knowledge and user preference I may be combined together to determine the best wake-up strategy to wake up the user.

Meanwhile, a relationship between an alarm impulse (alarm, vibration and etc.) and a user's reaction (the change in sleeping stage and status) is modeled by the Alarm-User Reaction (AUR) module (S908). In one embodiment, the Alarm-User Reaction (AUR) module may apply a multimodal deep regression algorithm to model the relationship between the alarm impulse (e.g., alarm, and vibration, etc.) and the user's reaction (e.g., the change in sleeping stage and status).

Figure 7:
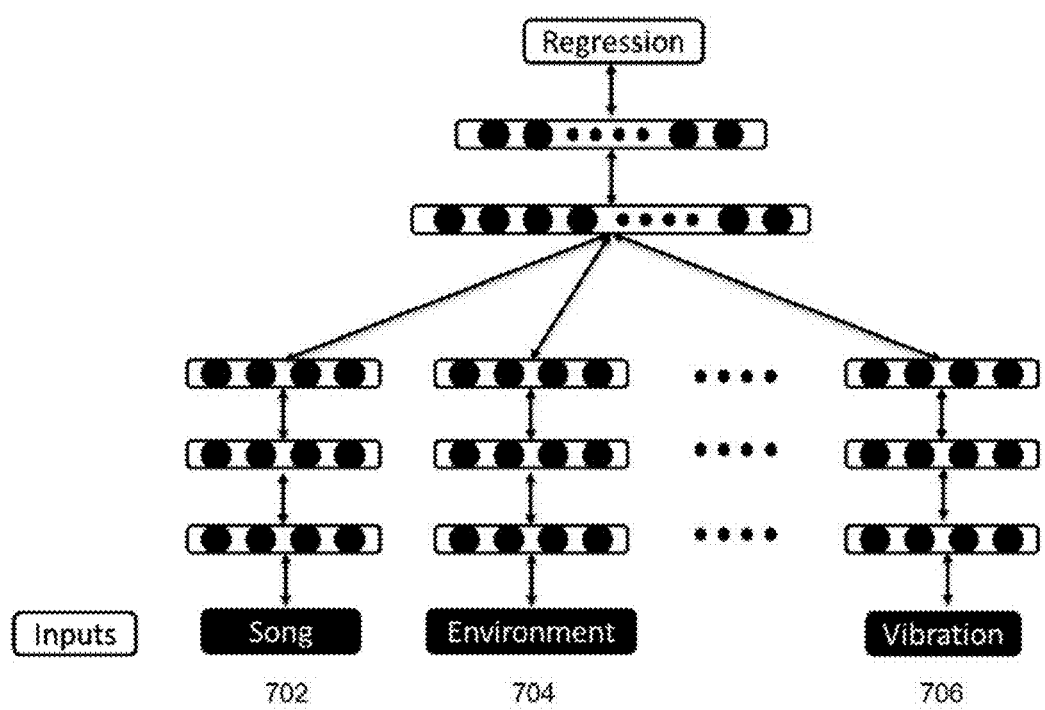
FIG. 7 illustrates an exemplary multimodal deep regression for alarm and user reaction modeling consistent with disclosed embodiments.

FIG. 7 illustrates an exemplary multimodal deep regression for alarm and user reaction (AUR) module consistent with disclosed embodiments. As shown in FIG. 7, after being trained with pre-collected data, a multimodal deep regression model or a multimodal deep neural network may be used to predict the response, namely the change in sleeping stage, by given a specific impulse. In one embodiment, the input of the multimodal deep regression model may be songs 702 chosen for wake-up alarms (i.e., alarm in songs), user's environment background 704, and vibrations (i.e., alarm in vibration) 706, etc.

Impulses of different types (e.g., alarm, vibration, a combination of alarm and vibration, etc.) and/or alarming in different ways (e.g., soft alarm, hard alarm, etc.) may lead to different user's reaction. For example, the types of the song chosen as wake-up alarms (i.e., the types of alarm in songs 702) may lead to different user's reaction, because light music may slightly wake the user up while rock music may be too stronger for a certain group of users. In addition, the ways to play the song alarm, such as playing with low/high volume, playing from low volume to high volume, playing in high/low frequency, may also have an impact on the user experience and may receive different user responses.

The environment background 704 may have to be taken into account as well. A constant or random noise, raised when someone is taking a shower on the next door, or when a truck is passing by, may also be considered as an alarm impulse, which may have an influence on the change in the user's sleeping stage. The vibration 706 may have the same effect as playing a sound alarm, and the vibration and sound alarm may also be combined.

Such different ways of waking the user up may have different signal types as inputs from different modalities, which may be the purpose of using the multimodal deep regression model shown in FIG. 7. That is, to embed all these possible ways and methods from different modalities and learn a joint representation in the deep hidden layer. The joint representation may be used as feature for further regression purposes. For example, the environmental background 704, measured by recording the background noise level through a built-in mic, may be a type of signal. To evaluate different ways of playing a sound, different chunks of songs of different types may be used, and audio signals may be extracted for each sample.

Audio signals may be not suitable to be fed into the regression model directly. However, features of the audio signals may be extracted to convert the audio signals to a signal in the frequency domain, for example, through Fourier Transform, or Mel-frequency cepstral coefficients (MFCCs) features may be extracted, which may be the same as a signal in the vibration domain. Any other potential possibilities modalities may also be adopted to convert the audio signals to a signal which is suitable to be fed into the multimodal deep regression model directly.

Figure 8:
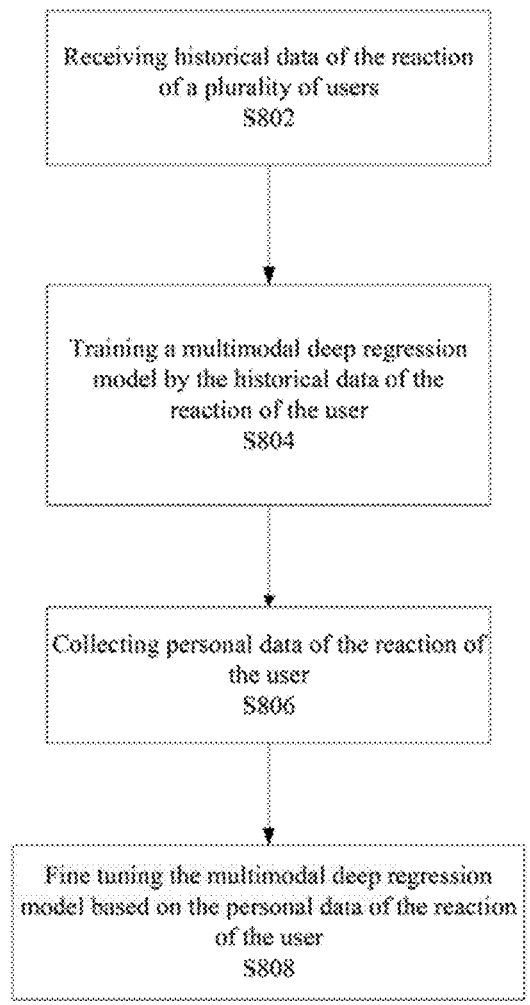
FIG. 8 illustrates a flow chart of an exemplary process of pre-training and fine-tuning for multimodal regression consistent with disclosed embodiments.

The multimodal deep regression model for the ARU module may be trained by the historical data or the pre-collected data, and may be further fine-tuned by the collected personal data. FIG. 8 illustrates a flow chart of an exemplary process of pre-training and fine-tuning for multimodal regression consistent with disclosed embodiments.

As shown FIG. 8, at the beginning, historical data of the reaction of a plurality of users is received (S802). The historical data may include various information of alarms and corresponding user actions previously collected or recorded by the system. The multimodal deep regression model is trained by the historical data or the pre-collected data (S804). Meanwhile, each individual user's data, i.e., personal data, may be collected by the system when the user is using the system (S806). The multimodal deep regression model is fine-tuned by the collected personal data (S808), i.e., a personalized regression model may be realized. Because the user reaction monitored by and received from the RSSD, as well as, the alarm impulse features are accurate, a robust multimodal deep regression model may be performed to the data. The AUR module may also be configured without collecting personalized data, but by fine-tuning the multimodal deep regression model with the personalized data and personalized optimization, a better performance of sensing how the individual user would react to a certain impulse may be obtained.

Returning to FIG. 9, after the optimized wake up strategy for the user is determined, a desired change in the user's current sleeping-stage for the current situation is identified (S910). Given the desired change, a best fit of a specific impulse is determined by the decision fusion (DF) module according to the multimodal deep regression model (S912), such as which song is going to be played, whether the song is played with or without vibration, and how the background noise is, etc.

The user preference II may also be fed into the decision fusion (DF) module to narrow down the searching of alarms. For example, some users may not like the songs to be played with a vibration, thus, such a vibration option may be removed. In addict, song lists and ratings from the user's Spotify, such as Apple music, and local music data base, etc., may also be embedded into the system, facilitating the search for the best alarm triggering strategy under the current situation. Given the alarm impulse candidates generated from the user preference II and the personalized intelligent wake-up system, and the relationship between an alarm impulse and the user's reaction estimated by the AUR module, a best move for the current situation may be found.

After the best fit of a specific impulse is determined, the alarm impulse is triggered by the decision fusion (DF) module (S914). The personalized intelligent wake-up system may keep monitoring the user's sleeping stage, especially the change in the sleeping stage for establishing the best wakeup strategy, and may go through the same work flow again until fully waking the user up. The monitoring data may be collected for the personalized fine-tuning as mentioned in the AUR module.

In the disclosed personalized intelligent wake-up system based on multimodal deep neural network, the robust sleeping stage detection (RSSD) module may perform a sleeping stage prediction based on historical data, and establish the best wakeup strategy by combining both user preference and prior knowledge. The alarm and user reaction (AUR) module may model the reaction of the user to a specific alarm impulse by applying the multimodal neural network for the regression modeling. The wake up strategy (WS) module may find the best strategy to wake up the user under the current situation, and the regression model may find the optimized alarm impulse to fulfill the WS strategy.

The disclosed intelligent wake-up system may provide an optimized wake-up alarm solution by applying the deep learning algorithms and combing the user preference input by the user and prior knowledge obtained from research studies on sleeping. The disclosed personalized intelligent wake-up system based on multimodal deep neural network is featured with personalized optimization for each individual user, the system reliability and the user experience may be significantly enhanced.

Those of skill would further appreciate that the various illustrative modules and method steps disclosed in the embodiments may be implemented as electronic hardware, computer software, or combinations of both. To clearly illustrate this interchangeability of hardware and software, various illustrative units and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The description of the disclosed embodiments is provided to illustrate the present invention to those skilled in the art. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for a personalized intelligent wake-up system based on multimodal deep neural network, comprising:
    monitoring a sleeping status of a user;
    obtaining a current sleeping-stage of the user within a current time frame and a prediction of a next sleeping-stage of the user for a next time frame;
    correcting the current sleeping-stage of the user through combining the current sleeping-stage and the prediction of the next sleeping-stage;
    based on the current sleeping-stage of the user, prior knowledge learnt from sleep-related research studies, and at least one user preference of waking up, determining a wake up strategy for the current time frame;
    determining a relationship between each of a plurality of alarm impulses adopted to wake up the user and a corresponding reaction of the user;
    identifying a change in the current sleeping-stage for the current time frame;
    based on the wake-up strategy established for the current time frame and the relationship between each of the plurality of alarm impulses and the reaction of the user, determining an alarm impulse to be triggered for waking up the user; and
    triggering the determined alarm impulse.

2. The method for a personalized intelligent wake-up system based on multimodal deep neural network according to claim 1, wherein obtaining a current sleeping-stage of a user within a current time frame further includes:
    receiving sensor date provided by a sensor capable of sensing body movements of the user during a sleep; and
    obtaining the current sleeping-stage of the user according to the sensor date.

3. The method for a personalized intelligent wake-up system based on multimodal deep neural network according to claim 2, wherein obtaining a prediction of a next sleeping-stage of the user for a next time frame further includes:
    receiving historical data of a plurality of users' sleeping status and personal data of the user sleeping status; and
    predicting the next sleeping-stage of the user based on a pre-trained sleeping-stage prediction according to the historical data and a personalized sleeping-stage prediction according to the personal data.

4. The method for a personalized intelligent wake-up system based on multimodal deep neural network according to claim 3, wherein:
    predicting the next sleeping-stage of the user based on a recursive neural network (RNN) model.

5. The method for a personalized intelligent wake-up system based on multimodal deep neural network according to claim 4, wherein correcting the current sleeping-stage of the user through combining the current sleeping-stage and the prediction of the next sleeping-stage further includes:
    correcting the current sleeping-stage of the user to obtain a corrected current sleeping-stage of the user through combing the sensor data, the pre-trained sleeping-stage prediction, and the personalized sleeping-stage prediction.

6. A method for a personalized intelligent wake-up system based on multimodal deep neural network, comprising:
    monitoring a sleeping status of a user;
    obtaining a current sleeping-stage of the user within a current time frame, comprising:
        receiving sensor date provided by a sensor capable of sensing body movements of the user during a sleep; and
        obtaining the current sleeping-stage of the user according to the sensor date;
    obtaining a prediction of a next sleeping-stage of the user for a next time frame, comprising:
        receiving historical data of a plurality of users' sleeping status and personal data of the user sleeping status; and
        predicting the next sleeping-stage of the user based on a pre-trained sleeping-stage prediction according to the historical data and a personalized sleeping-stage prediction according to the personal data;
    correcting the current sleeping-stage of the user through combining the current sleeping-stage and the prediction of the next sleeping-stage, comprising:

correcting the current sleeping-stage of the user to obtain a corrected current sleeping-stage of the user through combing the sensor data, the pre-trained sleeping-stage prediction, and the personalized sleeping-stage prediction;

based on the current sleeping-stage of the user, prior knowledge learnt from sleep-related research studies, and at least one user preference of waking up, determining a wake up strategy for the current time frame;

determining a relationship between each of a plurality of alarm impulses adopted to wake up the user and a corresponding reaction of the user;

identifying a change in the current sleeping-stage for the current time frame;

based on the wake-up strategy established for the current time frame and the relationship between each of the plurality of alarm impulses and the reaction of the user, determining an alarm impulse to be triggered for waking up the user; and triggering the determined alarm impulse;

wherein, the corrected current sleeping-stage of the user is calculated as:

$$S = \alpha S_{sensor} + (1-\alpha) S_{scaled}$$

where S denotes the corrected current sleeping-stage of the user, $S_{sensor}$ denotes the sensor data, $S_{scaled}$ denotes a scaled prediction of the user's sleep-stage, $\alpha$ denotes a weight.

7. The method for a personalized intelligent wake-up system based on multimodal deep neural network according to claim 6, wherein:

the weight $\alpha$ is calculated as $$\alpha = \frac{S_{wake} - S_{p'}}{2S_{wake} - S_{p'} - S_{s'}};$$

and the $S_{scaled}$ is calculated as $$S_{scaled} = \frac{S_{w'}}{S_{wake}} S_{predict},$$

where $S_{p'}$ denotes a last prediction of the user's sleeping-stage from the RNN model, $S_{s'}$ denotes a last inference of the user's sleeping-stage from the sensor data, $S_{wake}$ denotes a wake-up point stage of the user, $S_{w'}$ denotes a stage prediction of the wake-up point stage from a last available time frame, and $S_{predict}$ denotes a current prediction of the user's sleep-stage outputted from the RNN model.

8. The method for a personalized intelligent wake-up system based on multimodal deep neural network according to claim 1, wherein determining a relationship between each of a plurality of alarm impulses adopted to wake up the user and a corresponding reaction of the user further includes:

receiving historical data of the reaction of the plurality of users;

training a multimodal deep regression model by the historical data of the reaction of the user;

collecting personal data of the reaction of the user; and fine tuning the multimodal deep regression model based on the personal data of the reaction of the user.

9. A personalized intelligent wake-up system based on multimodal deep neural network comprising:

a robust sleeping-stage detection (RSSD) module configured to monitor a sleeping-stage of a user, obtain a current sleeping-stage of the user within a current time frame, predict a next sleeping-stage of the user for a next time frame, and correct the current sleeping-stage of the user;

a wake-up strategy (WS) module configured to receive to establish a wake-up strategy for the current time frame, based on the current sleeping-stage of the user, prior knowledge learnt from sleep-related research studies, and at least one user preference of waking up;

an alarm and user reaction regression (AUR) module configured to determine a relationship between each of a plurality of alarm impulses adopted to wake up the user and a corresponding reaction of the user; and a decision fusion (DF) module configured to determine an alarm impulse to be triggered based on the wake-up strategy established for the current time frame and the relationship between each of the plurality of alarm impulses and the reaction of the user, and configured to trigger the alarm impulse.

10. The personalized intelligent wake-up system based on multimodal deep neural network according to claim 9, wherein the RSSD module is further configured to:

receive sensor date provided by a sensor capable of sensing body movements of the user during a sleep; and obtain the current sleeping-stage of the user according to the sensor date.

11. The personalized intelligent wake-up system based on multimodal deep neural network according to claim 10, wherein the RSSD module is further configured to:

receive historical data of a plurality of users' sleeping status and personal data of the user sleeping status; and predict the next sleeping-stage of the user based on a pre-trained sleeping-stage prediction according to the historical data and a personalized sleeping-stage prediction according to the personal data.

12. The personalized intelligent wake-up system based on multimodal deep neural network according to claim 11, wherein the RSSD module is further configured to:

predict the next sleeping-stage of the user based on a recursive neural network (RNN) model.

13. The personalized intelligent wake-up system based on multimodal deep neural network according to claim 12, wherein the RSSD module is further configured to:

correct the current sleeping-stage of the user to obtain a corrected current sleeping-stage of the user through combing the sensor data, the pre-trained sleeping-stage prediction, and the personalized sleeping-stage prediction.

14. The personalized intelligent wake-up system based on multimodal deep neural network according to claim 9, wherein the AUR module is further configured to:

receive historical data of the corresponding reaction of the plurality of users to each of the plurality of alarm impulses adopted to wake up the plurality of users;

train a multimodal deep regression model by the historical data;

collect personal data of the corresponding reaction of the user to each of the plurality of alarm impulses adopted to wake up the user; and fine tune the multimodal deep regression model based on the personal data of the reaction of the user.

15. A non-transitory computer-readable medium having computer program for, when being executed by a processor, performing a method for a personalized intelligent wake-up system based on multimodal deep neural network, the method comprising:

monitoring a sleeping status of a user;

obtaining a current sleeping-stage of the user within a current time frame and a prediction of a next sleeping-stage of the user for a next time frame;

correcting the current sleeping-stage of the user through combining the current sleeping-stage and the prediction of the next sleeping-stage;

based on the current sleeping-stage of the user, prior knowledge learnt from sleep-related research studies, and at least one user preference of waking up, determining a wake up strategy for the current time frame;

determining a relationship between each of a plurality of alarm impulses adopted to wake up the user and a corresponding reaction of the user;

identifying a change in the current sleeping-stage for the current time frame;

based on the wake-up strategy established for the current time frame and the relationship between each of the plurality of alarm impulses and the reaction of the user, determining an alarm impulse to be triggered for waking up the user;

triggering the alarm impulse to wake up the user.

16. The non-transitory computer-readable medium according to claim 15, wherein obtaining a current sleeping-stage of a user within a current time frame further includes:

receiving sensor date provided by a sensor capable of sensing body movements of the user during a sleep; and obtaining the current sleeping-stage of the user according to the sensor date.

17. The non-transitory computer-readable medium according to claim 16, wherein obtaining a prediction of a next sleeping-stage of the user for a next time frame further includes:

receiving historical data of a plurality of users' sleeping status and personal data of the user sleeping status; and predicting the next sleeping-stage of the user based on a pre-trained sleeping-stage prediction according to the historical data and a personalized sleeping-stage prediction according to the personal data.

18. The non-transitory computer-readable medium according to claim 17, wherein:

predicting the next sleeping-stage of the user based on a recursive neural network (RNN) model.

19. The non-transitory computer-readable medium according to claim 18, wherein correcting the current sleeping-stage of the user through combining the current sleeping-stage and the prediction of the next sleeping-stage further includes:

correcting the current sleeping-stage of the user to obtain a corrected current sleeping-stage of the user through combing the sensor data, the pre-trained sleeping-stage prediction, and the personalized sleeping-stage prediction.

20. The non-transitory computer-readable medium according to claim 15, wherein determining a relationship between each of a plurality of alarm impulses adopted to wake up the user and a corresponding reaction of the user further includes:

receiving historical data of the reaction of the plurality of users;

training a multimodal deep regression model by the historical data of the reaction of the user;

collecting personal data of the reaction of the user; and fine tuning the multimodal deep regression model based on the personal data of the reaction of the user.

* * * * *